United States Patent
Morrin (10) Patent No.: US 9,250,434 B2
(45) Date of Patent: Feb. 2, 2016

(54) METHOD AND APPARATUS FOR AUTOMATIC FOCUSING OF SUBSTRATES IN FLOURESCENCE MICROSCOPY

(75) Inventor: Markus Morrin, Carlow (DE)

(73) Assignee: EUROIMMUN MEDIZINISCHE LABORDIAGNOSTIKA AG, Lubeck (DE)

(*) Notice: Subject to any disclaimer, the term of this patent is extended or adjusted under 35 U.S.C. 154(b) by 274 days.

(21) Appl. No.: 13/818,551

(22) PCT Filed: Aug. 23, 2011

(86) PCT No.: PCT/EP2011/004227
§ 371 (c)(1),
(2), (4) Date: Feb. 22, 2013

(87) PCT Pub. No.: WO2012/025220
PCT Pub. Date: Mar. 1, 2012

(65) Prior Publication Data
US 2013/0162804 A1    Jun. 27, 2013

(30) Foreign Application Priority Data

Aug. 23, 2010 (DE) .................. 10 2010 035 104

(51) Int. Cl.
| | |
|---|---|
| G06K 9/00 | (2006.01) |
| G02B 21/34 | (2006.01) |
| G02B 21/00 | (2006.01) |
| G02B 7/36 | (2006.01) |
| G02B 21/24 | (2006.01) |
| C12Q 1/00 | (2006.01) |
| G01N 21/64 | (2006.01) |

(52) U.S. Cl.
CPC *G02B 21/34* (2013.01); *G02B 7/36* (2013.01); *G02B 21/0004* (2013.01); *G02B 21/241* (2013.01); *G01N 21/6458* (2013.01)

(58) Field of Classification Search
USPC ......... 382/100, 103, 106, 108, 128–134, 154, 382/162, 168, 173, 181, 193–194, 199, 203, 382/219, 232, 254, 174, 176, 282–291, 305, 382/312, 321; 435/7.1, 6, 4; 250/252.1
See application file for complete search history.

(56) References Cited

U.S. PATENT DOCUMENTS

| | | | |
|---|---|---|---|
| 7,199,360 B1 * | 4/2007 | Montagu | 250/252.1 |
| 2004/0018523 A1 * | 1/2004 | Hawkins | 435/6 |
| 2005/0009101 A1 * | 1/2005 | Blackburn | 435/7.1 |
| 2008/0286750 A1 * | 11/2008 | Xu et al. | 435/4 |
| 2010/0151474 A1 * | 6/2010 | Afanasyev et al. | 435/6 |

* cited by examiner

Primary Examiner — Seyed Azarian
(74) Attorney, Agent, or Firm — Oblon, McClelland, Maier & Neustadt, L.L.P.

(57) ABSTRACT

An apparatus for automated examination of biological material (6) includes a microscope (8) with a cross table (9) with the biological material (6) being arranged on the cross table (9) between an object slide (1) or an analysis plate and a cover (4); a light source (15, 16); an evaluation unit; a device for automatic focusing (11); an image recording unit (17) for recording an image of the biological material (6) enlarged via of an object lens (10) of the microscope (8) and for transferring the image to the evaluation unit; and a biochip (2). Labeling (7) is provided on a surface of the biochip (2). Focusing is executable by targeted movement of the cross table (9) based on detection of the labeling (7), and a target interval is determinable by determination of a location and/or a position of the labeling, within which focusing of the biological material takes place.

20 Claims, 4 Drawing Sheets

METHOD AND APPARATUS FOR AUTOMATIC FOCUSING OF SUBSTRATES IN FLOURESCENCE MICROSCOPY

BACKGROUND OF THE INVENTION

The instant application should be granted the priority dates of Aug. 23, 2010, the filing date of the corresponding German patent application 102010035104.0, as well as Aug. 23, 2011, the filing date of the International patent application PCT/EP2011/004227.

The invention relates to a method as well as an apparatus for automated examination of biological material with a microscope, on the cross table of which the biological material is arranged between an object slide or an analysis plate and at least one cover, with at least one light source for exposure of the biological material as well as with an image recording unit recording at least one image of the biological material enlarged by means of the object lens of the microscope and transferring it to an evaluation unit. The technical solution described provides labeling, which is detectable by a device for automatic focusing of the biological material, wherein the focusing can be executed by targeted movement of the cross table taking the detection of the labeling as the basis.

In medical diagnostics, fluorescence microscopy represents a standard method for the examination of patient samples. In that, in this area, too, an attempt in respect of the further development of this technology consists in increasing the degree of automation in order to thus minimize the error probability and to improve the economic efficiency of microscopy.

In order to achieve an increase in the degree of automation at the laboratory, it is conceivable, on the one hand, to further automate the processing of the samples to be examined, in particular the dilution as well as the incubation steps, or, on the other hand, to design the process of the predominantly visual evaluation of the processed samples more effectively. The invention explained in more detail in the following lies in the field of sample evaluation or diagnostics, respectively, wherein also in respect of fluorescence microscopy it is already known in principle to generate digital image data of the samples to be examined and to transfer these to a data processing unit for the preparation of diagnostic findings, on which unit a special laboratory software is installed, and to evaluate the data in a computer-aided fashion.

With fluorescence microscopy at least partially automated in such manner, the generation and selection of high quality images is of outstanding significance, above all in order to be able to guarantee constantly high quality in the preparation of a laboratory result. A substantial quality feature of the recorded images ultimately is their sharpness, so that focusing of the biological material to be examined is of particular significance. For focusing of the biological material or the substrates, respectively, to be examined, usually a multitude of images is recorded at different levels, of which images those with low quality are discarded during the electronic evaluation.

In respect of automated focusing for microscopes, different technical solutions are known. In that, active autofocus systems, which are normally used in reflected-light microscopes, are characterized by the fact that using an auxiliary light source, a light spot or a marking is projected onto the surface of the sample to be examined or a cover slip covering the sample, then shape, position or size of the light spot are evaluated, and, on the basis of the evaluation, focusing on the sample or cover slip surface takes place. An active autofocus system designed in such manner is known, for example, from DE 34 46 727 C2, and is to enable fast automatic focusing.

In transmitted-light microscopes, passive autofocus systems are normally used instead of active ones. Passive autofocus systems, as, e.g., known from DE 34 39 304 C2, determine the focus level on the basis of a comparison of the recorded image data, i.e. the level, at which the sharpest image was recorded. Frequently, however, such systems are comparatively slow, since a multitude of search runs must be undertaken in order to achieve a satisfactory result.

A further special active autofocus system is known from DE 10 2010 035 104. In this printed publication, an apparatus for automatic focusing of weakly luminescent substrates is described, which is to guarantee fast image focusing. The comparatively fast focusing, on the one hand, is to increase the effectiveness of automatic microscopy and, on the other hand, minimize fading of the fluorescent dyes during focusing. The technical solution described is characterized by the fact that first, several recordings are undertaken in a transmitted-light mode, and therefrom the sharpest image is determined using known evaluation methods. Following switching-off of the transmitted-light source, the cross table of the microscope is moved to the focus level determined in the transmitted-light mode. In order to generate a fluorescence image, an excitation light source is then activated. Since, however, the fluorescence can vary at various levels in respect of the thickness of the substrate, it is necessary to still adjust the focus level in the fluorescence mode compared to the focus level determined in the transmitted-light mode on a regular basis. For determination of the exact focus level, however, due to the pre-focusing previously undertaken in the transmitted-light mode, only few images must be included in a comparatively small search area. The fluorescence images ultimately lying at the exact focus level are recorded by means of a digital camera and transferred to a data processing unit for the further preparation of diagnostic findings.

One objective of the further development of autofocus systems in fluorescence microscopy always is to minimize the time required for focusing or the number of images recorded during focusing and unusable for later examination of the substrate, respectively. For that, a further method for automatic focusing of a substrate in fluorescence microscopy is known from DE 101 00 247 A1, using which the object lens focus can be determined in a highly exact manner and still within a comparatively short period. In this case, an interference microscope is described, in which a surface of the object slide unit is provided with a coating detectable by light microscopy. The reflected light is detected by a detector, and on the basis of the detection signals, the phase position in the object area of the interference microscope is concluded. In this manner, it is finally possible to adjust the interference microscope in a suitable manner.

The microscopes with automatic or at least partially automated focusing previously described are frequently used to make special proteins visible by means of antibodies. In this manner, it is determined in which tissue a special protein exists and in which compartment of a cell it is located. Frequently, fixed tissue consisting of tissue sections is used for this antibody staining. Such tissue sections are generated by first preparing a frozen section of a healthy tissue and applying it to the surface of a glass slide, in particular an object slide or a cover slip. Subsequently, the tissue is thawed and dried. Normally, the tissue sections for the known test systems are attached to standard object slides, wherein for each tissue section, a separate standard object slide is used.

Beside the previously described possibility for examination of a patient sample using a tissue section arranged on a standard object slide, the so-called biochip technology of the company Euroimmun AG is known. Contrary to the conventional technology of indirect immunofluorescence, for which a tissue section is always attached to a standard object slide provided for the examination, this technology, due to a miniaturization of the samples to be examined, offers the possibility to standardize the determination of auto-antibodies and infection antibodies. In this manner, the work at the laboratory is facilitated and becomes more efficient.

The biochips of the company Euroimmun are comparatively small slides with biological material. In that, the effect is utilized, that very small tissue sections can be prepared and used for examination, provided that these are applied to a substrate carrying the section, and together with this substrate they are attached to an object slide or an analysis plate. While a standard cover slip is an about 100 µm to 200 µm thin, rectangular or round glass platelet, which usually has an area of 18×18 mm², biochips are cover slip fragments coated with suitable biological material, which thus have a much smaller surface. Therefore, compared to standard cover slips, biochips are on the one hand characterized by a distinctly lower space requirement, and on the other hand, the amount of tissue required is considerably reduced.

For the manufacture of a biochip, first a frozen section of the required tissue is likewise applied to a standard cover slip, then partially thawed and dried. Subsequently, the cover slip with the tissue is fragmented by producing score lines in the area of the tissue section using a diamond tip or a laser, along which the coated cover slip is broken and thus divided into segments. In order to enable an improved, in particular more effective examination, the biochips are applied to suitable reaction fields of an object slide. In this connection, it is conceivable to provide a multitude of reaction fields for respective biochips on one object slide, wherein in one reaction field, more than one biochip, preferably with different tissues, may also be provided. In order to design the examination of a patient sample particularly effective, suitable BIO-CHIP-Mosaiks™ are formed by providing a multitude of reaction fields with respective biochips on one object slide.

No matter, whether a tissue section located on a standard cover slip or a biochip or special BIOCHIP-Mosaiks™, respectively, is used for the examination of a patient sample, the basic course of sample processing, in particular dilution of the patient serum as well as incubation of the tissue section, as well as of the visual examination using a microscope is the same.

During processing of the sample, the tissue is incubated with diluted patient serum, which is to be examined for the presence of special antibodies, as well as a conjugate, which normally includes antibodies originating from an animal, which are marked with a fluorescent substance and directed against the antibodies suspected in the patient serum. If the patient serum has antibodies against the antigens of the tissue section, these antibodies bind to the tissue section and the fluorescently marked secondary antibodies bind to the human antibodies attached to the tissue section. Ultimately, the fluorescent dye bound to the respective tissue structures can be detected using a fluorescence microscope.

Prior to using the microscope, the incubated tissue section is coated with a mounting medium, like e.g. ph-buffered glycerin, and covered with a cover slip. The cover slip is arranged such that though it is located at a secure distance from the surface of the tissue section, viewing it with the microscope is still possible without any problem.

As already indicated, the objective for the further development of automatic apparatuses for the examination of patient samples principally consists in designing any procedural steps from receipt of the sample up to preparation of a laboratory result as efficient as possible, simultaneously eliminating possible sources of error as far as possible. Taking this general attempt of making laboratory work more effective and even more reliable as the basis, the present invention is based on the special object to further develop the technical solutions for automatic microscopy of biological material known from the state of the art such that automation of the microscopy of an object slide with biochips located thereon, in particular with BIOCHIP-Mosaiks, is possible in an advantageous manner. Above all, the process of focusing of the biological material arranged on the biochip(s) is to be realizable with comparatively simple means and simultaneously take place quickly as well as with high quality. The technical solution to be stated is to be easy to integrate into the known systems for automatic microscopy of biological material and represent an aid for the personnel working at the laboratory. A further object, on which the present invention is based, consists in minimizing the number of recordings made during focusing and not required later for image evaluation.

SUMMARY OF THE INVENTION

The invention relates to an apparatus for automated examination of biological material using a microscope, on the cross table of which the biological material is arranged between an object slide or an analysis plate and at least one cover, with at least one light source for exposure of the biological material as well as with an image recording unit recording at least one image of the biological material enlarged using the object lens of the microscope and transferring it to an evaluation unit, wherein labeling is provided, which can be detected by a device for automatic focusing of the biological material, and focusing can be performed by targeted movement of the cross table, taking the detection of the labeling as the basis, which has been further developed such that the biological material is arranged on a biochip manufactured by fragmentation and division of a cover slip, which biochip is applied to the object slide, and wherein the labeling is located on a side of the biochip facing the biological material.

With the technical solution according to the invention, it is ensured that focusing of the biological material arranged on the biochip takes place in a highly accurate and still comparatively quick fashion. Providing labeling on the biochip, which preferably is applied to the cover slip prior to division of the actual cover slip during the manufacture of the biochip already, easy and reliable focusing of the biological material is possible, as will be explained in more detail in the following. In that, the application of the labeling integrated into the manufacturing process of the cover slip offers the advantage that the labeling is substantially easier to apply to the not yet fragmented cover slip than to the comparatively small biochips.

It is essential for an effective focusing process that the labeling is located on that surface of the biochip, which compared to the surface of the biological material is relatively plane and thus enables an exact determination of distance. In that, in principle, it is possible to provide the labeling on a side of the biochip facing the biological material or on a rear side of the biochip facing away from this side.

In a first step immediately prior to the focusing process, detection of the labeling takes place, in particular determination of the distance between object lens and labeling. Based on the determination of the location and/or position of the labeling, in particular the distance between labeling and object lens, a target interval is determined. In that, the target interval has a maximum and a minimum distance to the object lens, between which the labeling and the material arranged on the surface of the biochip are located. In a special embodiment of the invention, following determination of the target interval, focusing of the biological material takes place within the target interval. Since in this manner, the search for the focus is restricted to the target interval, the focusing process can be considerably shortened.

Focusing of the labeling preferably takes place in a transmitted-light mode, which, among other things, has the advantage, that the biological material marked with fluorescent dyes is only briefly illuminated in the range of the excitation wavelength, and thus early fading of the fluorescent dye can be counteracted in a suitable manner.

Likewise, however, it is in principle conceivable to undertake focusing in the fluorescence mode. This is enabled by the focusing method according to the invention above all by the fact that the period required for the focusing process is shortened compared to known methods. Alternatively or in addition, for detection of the labeling, an auxiliary beam source, like e.g. a laser, is used. The beam of a laser used in such manner is preferably reflected by the labeling and received by a reception device. Thus, based on the evaluation of the beam path and/or runtime, a distance between the labeling and the object lens can be determined. This is possible because the auxiliary beam source, in particular the laser, is located in a defined position relative to the object lens.

As the labeling, which is detected by the device for focusing, a random pattern may be used. In an advantageous manner, grid lines are suitable, which at least in one direction of extension are equidistant. Such grid lines are applied to the cover slip or the biochip, respectively, prior to the biological material, which preferably is the frozen section of a tissue, being applied to the biochip. In that, the labeling is executed such that an influence between the labeling and the biological material applied to the biochip can be largely excluded.

A special further development of the invention provides that as the labeling of the biochip, at least three contours are provided, the center-points of which are equidistant. Such contours are detected by the device for focusing, so that the object lens of the microscope can be focused following focusing to the surface of the biochip or the biological material located thereon, respectively. In any case, using labeling provided on the biochip according to the invention, it is ensured that the location and/or position of the biochip, in particular the distance of the biochip surface from the microscope's object lens, is reliably detected. The contours provided on the biochip surface are preferably executed as circles, the center-points of which are equidistant. In this connection, it is conceivable that such labeling is applied to the surface of the biochip in the desired shape using a suitable apparatus, either prior to or following fragmentation of the cover slip. Likewise, however, it is conceivable to at least partially provide the surface with an extensive coating and to provide respective templates for the generation of the desired labeling, or to generate respective labeling contours following application of the extensive coating, e.g., by etching.

In a further embodiment of the invention, an area surrounding the labeling is determined, in which no images are recorded by the image recording unit and/or images recorded there are not used or discarded or deleted, respectively, in the evaluation unit during processing. Providing a respective area around the labeling provided on the biochip surface, it is guaranteed that tissue areas or cells, respectively, which possibly react with the labeling, are left unconsidered in the examination of the biological material or the diagnosis of a patient sample, respectively.

According to another further development of the invention, labeling is executed in the form of extensive coating of the biochip surface. In that, in an advantageous manner, in particular three areas of the biochip are provided with extensive labeling. In a very special further development, the entire surface of the biochip intended for labeling is provided with respective two-dimensional labeling. Using complete or partial extensive coating of the surface of the biochip, a respective signal is then generated in the distance sensor, likewise due to reflection or transmission at the layer.

In an advantageous manner, labeling comprising silicon is suited for detection during the work with an automatic microscope. Alternatively or in addition thereto, it is conceivable that the labeling comprises a metal, preferably chromium. Likewise, dielectric layers are conceivable, the spectral reflective properties of which are optimized for the distance sensor and do not have a negative impact on the image analysis. Should a metal or a dielectric be used for labeling on the biochip surface, it is conceivable to vapor-deposit or sputter it onto the surface. In respect of the manufacture of a respectively labeled biochip, this has the advantage that vapor deposition of metals can be undertaken reliably and relatively cost-effectively. In a special embodiment, here, too, special contours can be produced on the surface area provided with complete vapor deposition by etching.

According to a further embodiment of the invention, it is conceivable that the device for automatic focusing of the biological material has at least one laser light source or a polychromatic radiation source and a detector, which, at least partially, receives the light reflected by the labeling, and on the basis of the light received, generates a signal, which then is evaluated, and considering the evaluated signal, the targeted movement of the cross table takes place for focusing of the biological material. Upon using a laser light source as well as a detector, it is advantageously conceivable to coat the surface of the biochips at least partially with a metal, like e.g. chromium, and thus to reflect the laser beams. Using the described laser light source of the detector, it is possible, in an advantageous manner, to determine the location and/or position of the surface of the biochip, on which the biological material is arranged.

The invention is furthermore characterized by a method for automatic examination of biological material. The method according to the invention with a microscope, on the cross table of which the biological material is arranged between an object slide or an analysis plate and at least one cover, wherein the biological material is exposed to light, wherein with an image recording unit at least one image of the biological material enlarged by means of the object lens of the microscope is recorded and transferred to an evaluation unit, and wherein with a device for automatic focusing of the biological material, labeling is detected, a position and/or location of the labeling is determined and, on the basis of the detected position and/or location of the labeling, focusing of the biological material is undertaken by targeted movement of the cross table, has been further developed such that the biological material is provided on a biochip manufactured by fragmentation and division of a cover slip, which biochip is applied to the object slide, and the labeling is detected on a surface of the biochip.

An advantageous further development of the method according to the invention provides that, on the basis of the detected position and/or location of the labeling, a target interval is determined, within which the cross table is moved during focusing. Providing a target interval depending on the detected location and/or position of the biochip surface carrying the biological material, an interval can be determined in a preferred manner, which includes an area above and below the biochip surface. During the focusing process, the cross table is moved such that the focusing level is moved between the interval limits. Thus, in a preferred manner, the travel path of the cross table is restricted to a suitable value during focusing.

On the basis of the detected position and/or location of the labeling, the cross table is thus moved from at least one first position, in which the object lens has a first distance from the biological material, into a second position, in which the object lens has a second distance from the biological material, and furthermore, at least one image of the biological material is respectively recorded at two different levels between the first and the second position and transferred to the evaluation unit. In this connection, it is easily perceivable, that during the recording of at least two images at different levels, these have a different sharpness. Evaluating the images recorded within the target interval at at least two different levels with known image data evaluation methods, in a preferred manner, the image with the highest sharpness can be ultimately determined. Via the selection of the sharpest image, the focus level is then determined.

Thus, with the method described, it is possible in an advantageous manner to determine a focus level on the basis of a comparison of the recorded images in the evaluation unit. Those images recorded and likewise lying within the focus level are finally transferred to a device for preparing diagnostic findings. Preferably, this is a data processing unit, in particular a computer, on which laboratory software is installed. Using the laboratory software, the images recorded for a special patient sample are allocated to a patient dataset and respectively filed. A doctor responsible for the preparation of a diagnosis is thus enabled in a relatively easy manner to have any data in respect of the examined patient sample quickly displayed on a screen.

BRIEF DESCRIPTION OF THE DRAWINGS

In the following, the invention will be explained in more detail on the basis of embodiments without restriction of the general inventive idea on the basis of figures. In that, the figures show the following.

DETAILED DESCRIPTION OF THE PREFERRED EMBODIMENTS

Figure 1:
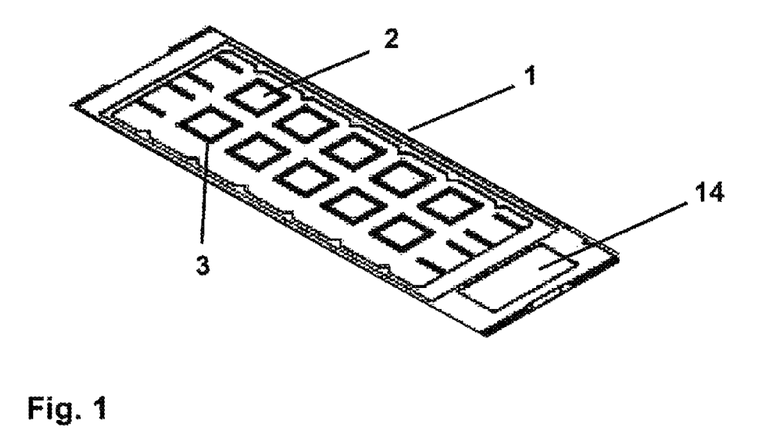
FIG. 1: Object slide with biochips.

FIG. 1 first shows an object slide 1 with biochips 2 arranged thereon. In that, the object slide 1 has ten reaction fields 3, which compared to the remaining surface of the object slide 1 are executed as small depressions. The biochips 2 are arranged on the reaction fields 3. In principle, it is conceivable to provide one or even several biochips 2 on one reaction field 3. In this connection, it is self-evidently possible to adjust the size of the reaction field 3 in a suitable manner.

The biochips 2 are small slides with biological material, which were manufactured by coating of a standard cover slip with a tissue section and subsequent fragmentation of the cover slip. While a standard cover slip is an about 100 μm to 200 μm thin, rectangular or round glass platelet, which usually has an area of 18×18 $mm^2$, biochips 2 are cover slip fragments coated with suitable biological material, which thus have a much smaller surface. Depending on the respective examination profile as well as the customer request, on an object slide 1, a multitude of reaction fields 3 can be provided for respective biochips 2. In that, it is likewise conceivable to provide more than one biochip with different tissues on one reaction field 3.

During an examination at the laboratory, the tissue sections arranged on the reaction fields 3 of the object slide 1 and covered with tissue are incubated with different fluids, in particular a patient sample. Following completion of incubation and prior to using the microscope, the incubated tissue section is coated with pH-buffered glycerin as a mounting medium and covered with a cover slip 4. The cover slip 4 is arranged such that though it is located at a secure distance from the surface of the tissue section, viewing with the microscope is still possible without any problem.

Figure 2:
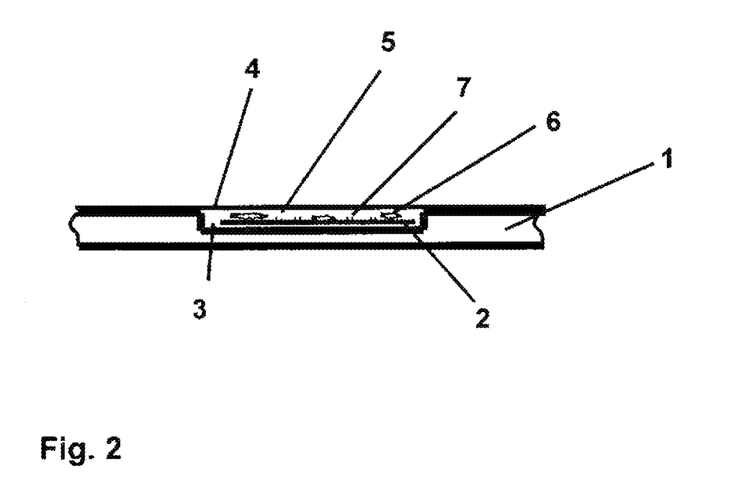
FIG. 2: Sectional view of the reaction field of an object slide with biochips.

FIG. 2 shows a highly enlarged sectional view of a reaction field 3 of an object slide 1. On the reaction field 3 of the object slide 1, a biochip 2 coated with part of a tissue section 6 is located. The tissue section is coated with a mounting medium 5 and covered by a cover slip 4. On the side facing the microscope, the surface of the biochip 2 carrying the tissue section 6 is provided with labeling 7 in the form of lines.

Figure 3:
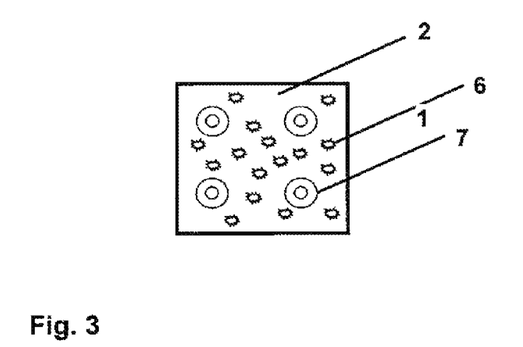
FIG. 3: Top view on a biochip with labeling.

In addition to that, in FIG. 3, the biochip 2 arranged on the reaction field 3 of the object slide is shown in a top view. The lines used as the labeling 7 are arranged on the surface in groups of several concentric circles. Upon using the microscope, the labeling 7 can be detected by means of an apparatus for automatic focusing of the biological material 6 located on the biochip, and focusing is performed. Optionally, the extension of the labeling 7 in the z-direction is considered during the focusing process in order to achieve an optimization of focusing. Thus, the labeling provided on the biochip 2 serves detection of the focus level. It is essential for the labeling 7 not to react with the biological material 6 located on the biochip 2.

Alternatively to the version of the labeling 7 in the form of groups of concentric circles represented in FIG. 3, it is conceivable to apply parallel lines or a grid pattern onto the surface of the biochip 2. Likewise, two-dimensional labeling 7, in particular with a metal or dielectric, is possible.

Furthermore, labeling 7 provided according to the invention can either be provided on the top side of the biochip 2, i.e. on the side facing the tissue 6 located thereon, or on the rear side, i.e. on the surface facing the object slide 1. It is respectively essential that the labeling 7 can be reliably detected by the apparatus for automatic focusing of the biological material 6 located on the biochip 2. Furthermore, depending on the version and arrangement of the labeling 7, the extension of the labeling 7 in the z-direction and/or the thickness of the biochip 2 carrying the tissue are considered in determining the focus level.

For examination of a patient sample, an object slide 1 according to FIG. 1 is provided, equipped with a multitude of biochips 2 covered with a cover slip 4. In that, different tissues 6 or biological material, respectively, are located on the various biochips 2. The object slide 1 with the biochips 2 is placed on the cross table 9 of a microscope 8 and fixed there. In this connection, it is conceivable that the object slide 1 is positioned on the cross table 9 manually or by means of a handling apparatus 13. In particular for microscopes 8, which are operated at an at least partially automated laboratory, the incubated object slides 1 with the biochips 2 are stored in suitable object slide boxes 12 and moved in an automated fashion between these and the cross table 9 by means of a handling apparatus 13. A suitable handling apparatus 13 preferably has a gripper, wherein the gripper is mobile either relative to the cross table 9 or together with the cross table.

In any case, the object slides 1 have markings 14 in the form of an inscription or a code, which enable exact identification of the patient sample located on the biochips 2 as well as preferably also of the tissue types located on the biochips 2.

Figure 4:
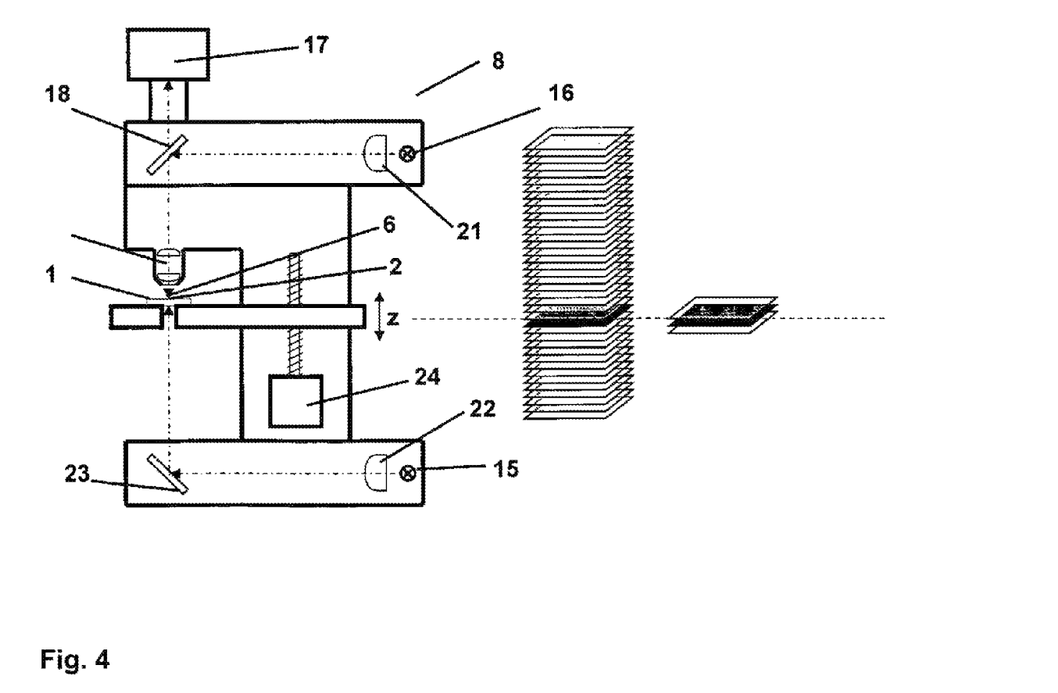
FIG. 4: Schematized representation of a microscope with automated focusing.

FIG. 4 shows a schematic representation of a fluorescence microscope 8 with a transmitted-light device, a vertically movable cross table 9, and a digital camera 17 for image recording. Furthermore, an excitation light device with a dichromatic beam splitter 18 and an excitation light source 16 is provided. The beam splitter 18 reflects the excitation light emitted by the excitation light source 16 in the direction towards the biological material 6 arranged on the biochip 2. Contrary to that, the transmitted-light emitted by the transmitted-light source 15 and redirected by a deflecting mirror 23 from the direction of the biochip 2 with the biological material 6 is being let through. The dichromatic beam splitter 18 is preferably executed as a reflection pass filter and reflects all wavelengths below 510 nm. Expressed in a simplified manner, the dichromatic beam splitter 18 thus acts as a deflecting mirror for the excitation light, while the light with the wavelength of fluorescence passes the beam splitter 18 unhinderedly. In addition to the beam splitter or the reflection pass filter 18, respectively, which completely reflects the excitation light, a long pass blocking filter 19 is preferably also provided, which filters out light with wavelengths below 510 nm.

In the embodiment described here, the fluorescent dye fluorescein is used, the absorption maximum of which lies at 485 nm and the emission maximum at 514 nm. One substantial aspect of the technology described must be seen in the fact that the digital camera 17, arranged behind the long pass blocking filter 19 in the direction of the beam path, must record images in the fluorescence mode as well as images in transmitted-light mode. For this reason, the transmitted-light source 15 is executed as a LED with a wavelength of 520 to 535 nm. Light of this wavelength passes the beam splitter 18 as well as the blocking filter 19.

For the focusing process, the transmitted-light device generates light with a wavelength in the range of the emission wavelength of the fluorescent dye by means of the transmitted-light source 15. For that, the light emitted by the transmitted-light source 15 is focused by suitable optics 22 and subsequently deflected vertically upward by the deflecting mirror 23 in order to radiate through the biochip 2 with the biological material 6 located thereon from below.

The material 6 applied on the biochip 2 is, for example, cultivated human epithelial cells, to which antibodies against cell cores are bound, which were stained with fluorescein-marked anti-human antibodies. Since the absorption maximum, i.e. the excitation wavelength of the fluorescein, is 485 nm, the dye is not excited for fluorescence by the transmitted light.

As can be further retrieved from FIG. 4, the transmitted light emitted by the transmitted-light source 15 in the horizontal direction, is first bundled by the optics 22, and thereafter deflected in the vertical direction by the deflecting mirror 23. The transmitted light passes the biochip 2 with biological material 6 arranged on the cross table 9, is bundled by the object lens 20 of the microscope 8, and passes, unhinderedly, the dichromatic beam splitter 18 as well as the long pass blocking filter 19, in order to then get to the sensor of the digital camera 17. The digital camera 17 records the image of the cell walls of the biological material 6 generated with the transmitted light with a relatively short exposure period of about 10 ms.

In order to minimize the number of images required for focusing in the transmitted-light mode recorded at various levels vertical to the z-axis, the biochip 2 has labeling 7 on its surface, and the microscope 8 is provided with a device for detecting this labeling. Prior to the start of the focusing process in the transmitted-light mode, now first the distance of the labeling 7 from the object lens 20 and/or its location relative to the object lens 20 is determined. For that, a light or beam source, respectively, emitting light is provided, which light is finally reflected by the labeling 7 and detected by a suitable sensor. Considering the runtime and/or the beam path, the distance of the labeling 7 from the object lens 20 and/or its location relative to the object lens 20 is determined. Optionally, in the determination of the distance and/or the location stated above, the thickness of the labeling 7, i.e. its extension in the z-direction, too, is considered. Considering the determined distance of the labeling 7 from the object lens, the cross table 9 is moved in the z-direction by means of a motor 24 such that focusing in the transmitted-light mode is only performed within a certain target range. Within this target range, which represents a distance interval of a few micrometers in the z-direction, in the transmitted-light mode, a few, preferably three images are recorded at different levels. Subsequent thereto or at least partially simultaneously, values for the respective sharpness of each individual image are determined by a connected data processing system (not shown), using the known sum-modulus-difference (SMD) method. That image, for which this value is the maximum, is identified as the sharpest image, and the associated vertical position (in the z-direction) of the cross table is determined as the focus level.

Independent of the type and version of the labeling on the biochip, areas of the images, mapping the near-field of the labeling, are preferably not considered in the determination of the focus level. This takes place in order to ensure that parts of the biological material 6 located on the biochip 2, which could be affected by the labeling, are not considered in the evaluation.

Once the transmitted-light source 15 was switched off, the cross table 9 is moved to the focus level determined in the transmitted-light mode. In order to generate a fluorescence image, the excitation light source 16 executed as a LED is then switched on. The emitted light is focused by suitable optics 21 and hits the dichromatic beam splitter 18 already described, which reflects the excitation light downwardly, and thus deflects it through the object lens 20 onto the biological material 6 on the biochip 2. There, the excitation light hits the fluorescent dye, which due to this excitation emits diffuse light with a main wavelength of 514 nm. A small part of this fluorescent radiation is emitted in a vertically upward direction, runs through the object lens 20, and passes the dichromatic beam splitter 18 as well as the long pass blocking filter 19, in order to be recorded by the digital camera 17.

Due to a long exposure time of about 500 ms, the camera 17 generates a fluorescence image. Since the location of the fluorescence varies within the height of the biological material 6, the focus level in the fluorescence mode may deviate compared to the focus level found in the transmitted-light mode. In order to determine the exact focus level, now a number of fluorescence images are also recorded in a search area, which has a size of only a few micrometers. Thus, just like in the transmitted-light mode, the cross table position is changed using a motor in the vertical direction (z-direction) for each image. Using the sum-modulus-difference (SMD) method, the fluorescence image with the highest sharpness is determined.

Due to the initially undertaken focusing in the transmitted-light mode, the area, in which the focus level in the fluorescence-mode must be determined, is comparatively small. In this manner, the time in which the fluorescent dye is excited to emit radiation and therefore at least partially consumed, can be minimized. In addition to that, the exposure times in the transmitted-light mode are considerably shorter than in the fluorescence mode. In order to achieve a further reduction of the time required for auto-focusing, using the labeling 7 provided on the biochip, it is ensured that only few, preferably 3 images must be recorded in the transmitted-light mode. Without providing respective labeling, about 100 images are usually recorded in the transmitted-light mode during focusing. Thus, considering the respective exposure time, the duration of transmitted-light focusing is reduced from 100×10 ms=1 s to 3×10 ms=30 ms.

If the entire auto-focusing process was executed in fluorescent light, the duration of focusing would even increase to about 200×500 ms=100 s. Even when due to the long exposure time in the fluorescence mode the calculations for the image sharpness (SMD) can take place in parallel to image recording, and therefore image recording can be interrupted as soon as the sharpest image was found, on average, a summed up exposure time of about 50 s would still be required.

Figure 5:
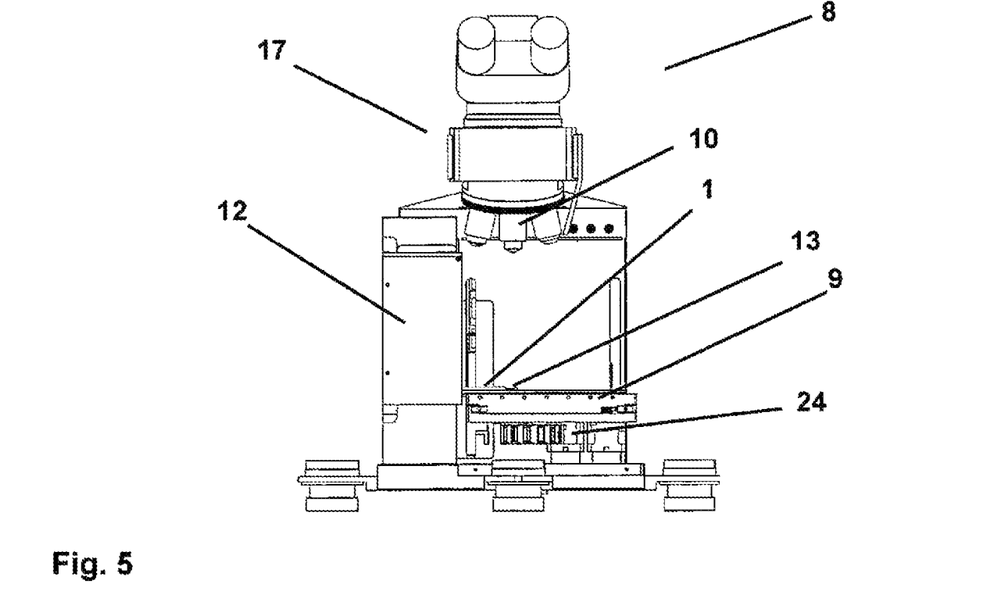
FIG. 5: Front view of a microscope with automated focusing.
Figure 6:
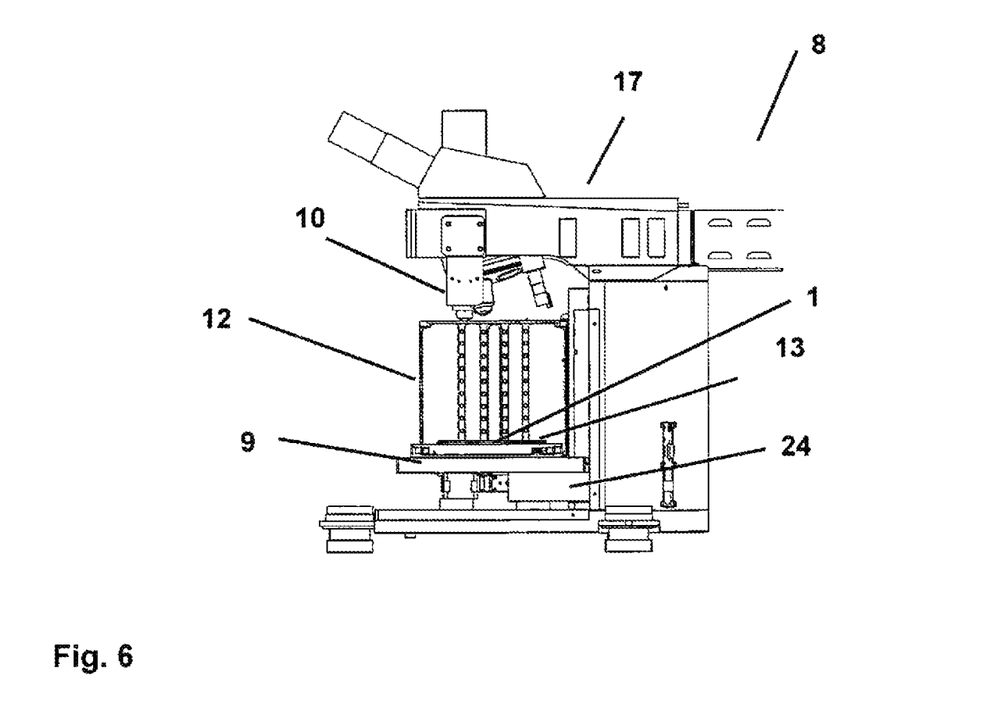
FIG. 6: Lateral view of a microscope with automated focusing; as well as
FIG. 7: Isometric view of a microscope with automated focusing.
Figure 7:
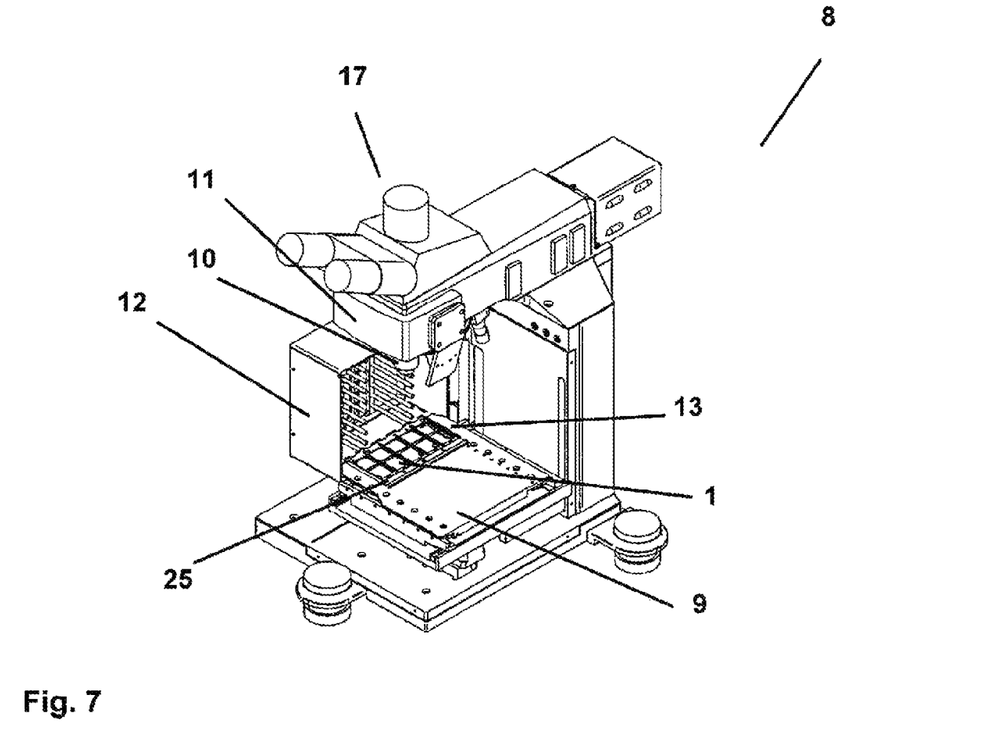

FIGS. 5, 6 and 7 respectively show a fluorescence microscope 8 for automated examination of biological samples 6. Equal components are provided with the same reference numbers. The microscope 8 represented is equipped with a device for automatic focusing of the biological material 6, which is executed such that it detects labeling 7 provided on the biochips 2 arranged on the object slides 1, and on the basis of this detection determines a target range in the z-direction, within which the focus level is located. For exact determination of the focus level, only few image recordings are required, so that compared to known systems, automatic focusing can be considerably accelerated.

The fluorescence microscope 8 has a take-up, at which an object slide box 12 can be fastened, which serves storing and providing several object slides 1. Using a handling apparatus 13, which is executed as a gripper fastened to the cross table 9, the object slides 1 required for an examination can be taken from the object slide box 12 in a targeted fashion and subsequently returned there. The object slide box 12 as well as the individual object slides 1 have a marking in the form of an inscription or a code in order to respectively guarantee clear identification. Provision, processing and examination of the samples are controlled using laboratory software, via which the examination results are saved and issued, too.

For preparation of the microscope process, a so-called carrier 25, in which the required object slides 1 are held, is taken from the object slide box 12 and fixed in the desired position on the cross table 9 using the handling apparatus 13.

Figure 8:
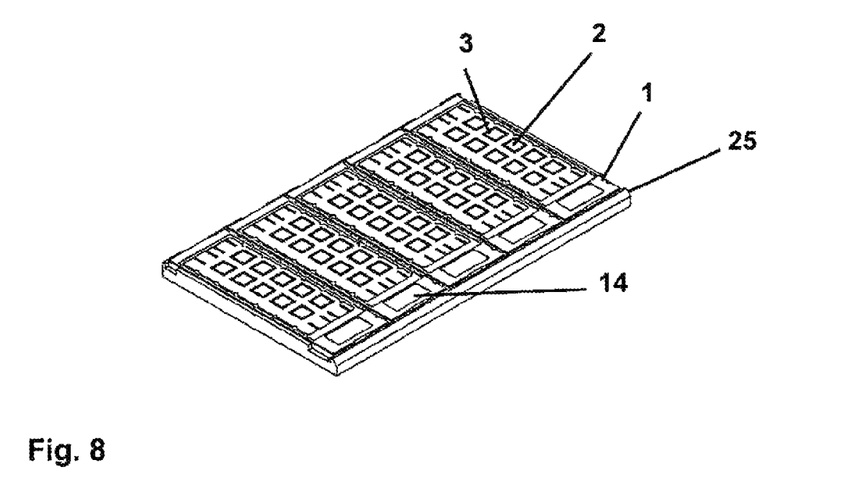
FIG. 8: Carrier for multiple object slides.

An example of the design of the carrier 25 is shown in FIG. 8. The carrier 25 shown is executed in a frame shape and has five take-ups for object slides 1. The object slides 1 with the biochips 2 arranged thereon on respectively ten reaction fields 3, are safely held by the carrier 25 and in this manner can be reliably stored and transported.

Following removal of a carrier 25 from the object slide box 12 by the handling apparatus 12 in the form of a gripper, positioning takes place such that ultimately the biochip 2 intended for examination is located underneath the object lens 10 of the microscope. Above the object lens 20, the digital camera 17 is located, using which the required images are recorded. The arrangement of the transmitted-light source as well as the excitation light source 15, 16 as well as the further optical elements corresponds to that explained in connection with the description of FIG. 4.

The auto-focusing process described already, including detection of the labeling 7 on the biochips as well as recording of images at different levels, first takes place in a central area of the respectively examined biochip. Subsequent to that, further focusing and image recording associated therewith is undertaken in two further areas of the biochip 2, which are located to the left or right, respectively, of the centre. For that, the cross table 9 is respectively moved in the horizontal direction.

It is respectively essential that upon focusing, first the labeling 7 on the biochips 2 is detected, in order to thus restrict the horizontal area, where the focus level is to be expected, in a reasonable manner, and to optimize the automated focusing process in respect of the time required.

The specification incorporates by reference the disclosure of DE 10 2010 035 104.0, filed Aug. 23, 2010, as well as International application PCT/EP2011/004227, filed Aug. 23, 2011.

The present invention is, of course, in no way restricted to the specific disclosure of the specification and drawings, but also encompasses any modifications within the scope of the appended claims.

LIST OF REFERENCE NUMBERS

1 Object slide
2 Biochip
3 Reaction field
4 Cover slip
5 Mounting medium
6 Biological material
7 Labeling
8 Microscope
9 Cross table
10 Object lens
11 Apparatus for automated focusing
12 Object slide box
13 Handling apparatus
14 Marking
15 Transmitted-light source
16 Excitation light source
17 Digital camera
18 Dichromatic beam splitter
19 Long-pass blocking filter
20 Object lens
21 Optics of the excitation light source
22 Optics of the transmitted-light source
23 Reflecting mirror
24 Motor
25 Carrier

The invention claimed is:
1. An apparatus for automated examination of biological material, comprising:
a microscope equipped with a moveable cross table;
a device for automatic focusing of the microscope by movement of the cross table;
a light source;
an image recording unit adapted to record at least one image enlarged by an object lens of the microscope;

an image evaluation unit in communication with the image recording device;

wherein an object slide or an analysis plate having at least one biochip and at least one cover arranged thereon is located on the moveable cross table in a focal range of the object lens, the biochip comprises a surface having labeling detectable by the automatic focusing device and a surface for application of the biological material to be examined such that focusing of the object lens on the biological material is accomplished by focusing of the labeling, and focusing of the labeling is obtained by movement of the cross table by the focusing device such that a target interval of the labeling is arranged by at least one of a location of the labeling and a position of the labeling in the object range, and wherein the biochip is manufactured by fragmentation and division of a cover slip.

2. The apparatus according to claim 1, wherein the labeling of the biochip comprises a grid line pattern.

3. The apparatus according to claim 1, wherein the labeling of the biochip comprises at least three contours, wherein a center-point of each contour is equidistant from the other center points.

4. The apparatus according to claim 3, wherein the contours are circles.

5. The apparatus according to claim 1, further comprising an area surrounding the labeling, wherein no images are recorded or if recorded images are present, the images are not focused by the object lens during processing in the evaluation unit.

6. The apparatus according to claim 1, wherein the labeling covers at least a section of the biochip surface.

7. The apparatus according to claim 1, wherein the labeling covers that side of the biochip facing the biological material.

8. The apparatus according to claim 1, wherein the labeling comprises silicon.

9. The apparatus according to claim 1, wherein the labeling comprises a metal.

10. The apparatus according to claim 1, wherein the labeling comprises a dielectric.

11. The apparatus according to claim 1, wherein the labeling comprises chromium.

12. The apparatus according to claim 1, wherein the labeling is vapor-deposited and/or sputtered onto said biochip.

13. The apparatus according to claim 1, wherein the device for automatic focusing of said biological material comprises:

a laser radiation source or a polychromatic radiation source, and a detector configured to receive the radiation reflected by the labeling and generate a signal on the basis of the received radiation, wherein the received radiation is evaluated, and the targeted movement of the cross table takes place for focusing of the labelling.

14. A method for automated examination a biological material with microscope performed with a processor, comprising:

arranging the biological material on a moveable cross table of the microscope between an object slide having at least one biochip or an analysis plate having at least one biochip and at least one cover, wherein the biochip comprises a surface having labeling detectable by an automatic focusing device and a surface for application of the biological material to be examined;

exposing the biological material to light to form an image of the biological material in the microscope;

automatically focusing the image of the biological material that is enlarged with an object lens of the microscope by movement of the cross table by the focusing device such that a target interval of the labeling of the biochip is arranged by at least one of a location of the labeling and a position of the labeling in the focal range;

transferring the focused image to an evaluation unit; and preparing a diagnostic evaluation of the biological material from analysis of the automatically focused image;

wherein the biochip is manufactured by fragmentation and division of a cover slip.

15. The method according to claim 14, wherein, on the basis of at least one selected from the group consisting of a detected position of the labeling and a detected location of the labeling, a target range is determined, within which the cross table is moved during focusing.

16. The method according to claim 14, wherein, on the basis of at least one selected from the group consisting of a detected position of the labeling and a detected location of the labeling, the cross table is moved from a first position, in which the object lens has a first distance from the biological material, into a second position, in which the object lens has a second distance from the biological material, and at two different levels between the first and the second position, at least one image of the biological material is taken and transferred to the evaluation unit.

17. The method according to claim 14, wherein a light employed for detection of the labeling has a different wavelength from a light employed for exposure of the biological material.

18. The method according to claim 15, wherein, during focusing and while the cross table is located within the target range, the biological material is exposed to light and at least one image of the biological material is recorded at two different levels within the target range and transferred to the evaluation unit.

19. The method according to claim 14, wherein a focus level is determined based on a comparison of the recorded images in the evaluation unit.

20. The method according to claim 19, wherein images lying at the focus level are transferred to a device for the preparation of the diagnostic evaluation.

* * * * *